(12) United States Patent
Bergersen

(10) Patent No.: US 7,975,701 B2
(45) Date of Patent: Jul. 12, 2011

(54) APPLIANCE, SYSTEM AND METHOD FOR CORRECTION HABITS OF AN ORAL CAVITY

(75) Inventor: Earl O. Bergersen, Dorado, PR (US)

(73) Assignee: Ortho-Tain, Inc, Dorado, PR (US)

( * ) Notice: Subject to any disclaimer, the term of this patent is extended or adjusted under 35 U.S.C. 154(b) by 37 days.

(21) Appl. No.: 11/729,674

(22) Filed: Mar. 28, 2007

(65) Prior Publication Data

US 2007/0240724 A1 Oct. 18, 2007

Related U.S. Application Data

(60) Provisional application No. 60/792,729, filed on Apr. 18, 2006.

(51) Int. Cl.
*A61C 5/14* (2006.01)
*A61F 5/56* (2006.01)
(52) U.S. Cl. ............. 128/859; 128/848; 128/861; 433/6
(58) Field of Classification Search .................. 128/859, 128/860, 861, 862, 848; 433/6; 600/24; 602/902
See application file for complete search history.

(56) References Cited

U.S. PATENT DOCUMENTS

| | | | |
|---|---|---|---|
| 3,510,946 A | 5/1970 | Kesling |
| 3,724,075 A | 4/1973 | Kesling |
| 3,837,081 A | 9/1974 | Kesling |
| 3,950,851 A | 4/1976 | Bergersen |
| 4,073,061 A | 2/1978 | Bergersen |
| 4,105,032 A | 8/1978 | Blomstedt |
| 4,139,944 A | 2/1979 | Bergersen |
| 4,370,129 A | 1/1983 | Huge |
| 4,371,336 A | 2/1983 | Hilleman |
| 4,396,373 A | 8/1983 | Dellinger |
| 4,448,735 A | 5/1984 | Huge |
| 4,568,280 A | 2/1986 | Ahlin |
| 4,580,975 A | 4/1986 | Schrems et al. |
| 4,591,341 A | 5/1986 | Andrews |
| 4,784,605 A | 11/1988 | Bergersen |
| 4,793,803 A | 12/1988 | Martz |
| 4,799,884 A | 1/1989 | Bergersen |
| 4,830,612 A | 5/1989 | Bergersen |
| 4,898,535 A | 2/1990 | Bergersen |

(Continued)

*Primary Examiner* — Patricia M Bianco
*Assistant Examiner* — Keri J Nelson
(74) *Attorney, Agent, or Firm* — Patents+TMS, P.C.

(57) ABSTRACT

An appliance, a system and a method correct habits of an oral cavity of a patient. The appliance is preformed or is custom-made in an open position or in a closed position. The appliance prevents the patient from breathing through an oral cavity of the patient and encourages the patient to breathe through a nose of the patient. The appliance corrects abnormal swallowing patterns, finger sucking habits, thumb sucking habits, abnormal tongue posturing, abnormal lip posturing and/or speech problems. A slot is formed on a top portion of the appliance to receive teeth of the patient for wearing the appliance. A shelf is formed on a bottom portion of the appliance to move a tongue of the patient to a correct position within the oral cavity during swallowing movements and/or during resting periods between the swallowing movements since there is more room above the shelf from a hollow area above of the shelf which is more comfortable for the patient. First projections are formed on the appliance which may contact the tongue to move the tongue to the correct position within the oral cavity. Second projections are formed on the appliance which may contact the tongue to prevent tongue thrusting by the tongue during the resting periods and/or during the swallowing movements. Third projections are formed on the appliance to move lips to a closed position during resting periods and/or the swallowing movements.

20 Claims, 1 Drawing Sheet

U.S. PATENT DOCUMENTS

| | | |
|---|---|---|
| 4,919,612 A | 4/1990 | Bergersen |
| 4,983,334 A | 1/1991 | Adell |
| 4,986,751 A | 1/1991 | Bergersen |
| 5,028,231 A | 7/1991 | Hall |
| 5,037,294 A | 8/1991 | Bergersen |
| 5,037,295 A | 8/1991 | Bergersen |
| 5,042,506 A | 8/1991 | Liberati |
| D323,215 S | 1/1992 | Bergersen |
| 5,092,346 A * | 3/1992 | Hays et al. .................... 128/848 |
| 5,328,362 A | 7/1994 | Watson et al. |
| 5,334,218 A | 8/1994 | Johnson |
| 5,338,190 A | 8/1994 | Tregillis |
| 5,536,168 A | 7/1996 | Bourke |
| 5,624,257 A * | 4/1997 | Farrell ............................ 433/6 |
| 5,645,420 A | 7/1997 | Bergersen |
| 5,683,244 A | 11/1997 | Truax |
| 5,779,470 A | 7/1998 | Kussick |
| 5,807,100 A | 9/1998 | Thornton |
| 5,814,074 A | 9/1998 | Branam |
| 5,816,799 A | 10/1998 | Parker |
| 5,876,199 A | 3/1999 | Bergersen |
| 5,882,192 A | 3/1999 | Bergersen |
| 5,911,576 A | 6/1999 | Ulrich et al. |
| 5,975,893 A | 11/1999 | Chishti et al. |
| 6,129,084 A | 10/2000 | Bergersen |
| 6,183,248 B1 | 2/2001 | Chishti et al. |
| 6,247,926 B1 | 6/2001 | Thornton |
| 6,299,440 B1 | 10/2001 | Phan et al. |
| 6,302,686 B1 | 10/2001 | Chott et al. |
| 6,454,565 B2 | 9/2002 | Phan et al. |
| 6,467,484 B1 * | 10/2002 | De Voss ........................ 128/848 |
| 6,505,625 B1 | 1/2003 | Uenishi |
| 6,572,372 B1 | 6/2003 | Phan et al. |
| 6,582,225 B1 | 6/2003 | Bergersen |
| 2002/0187451 A1 | 12/2002 | Phan et al. |
| 2003/0111083 A1 * | 6/2003 | Bancroft ...................... 128/859 |
| 2003/0224312 A1 | 12/2003 | Bergersen |
| 2003/0224313 A1 | 12/2003 | Bergersen |
| 2003/0224314 A1 | 12/2003 | Bergersen |
| 2003/0225594 A1 | 12/2003 | Bergersen |
| 2004/0058295 A1 | 3/2004 | Bergersen |
| 2004/0152032 A1 | 8/2004 | Bergersen |
| 2005/0037311 A1 | 2/2005 | Bergersen |
| 2005/0072435 A1 * | 4/2005 | Eubank ........................ 128/861 |
| 2005/0241646 A1 * | 11/2005 | Sotos et al. .................. 128/848 |

* cited by examiner

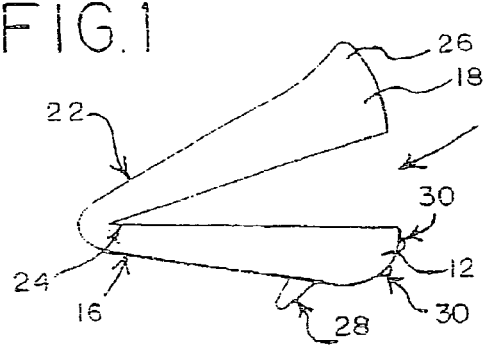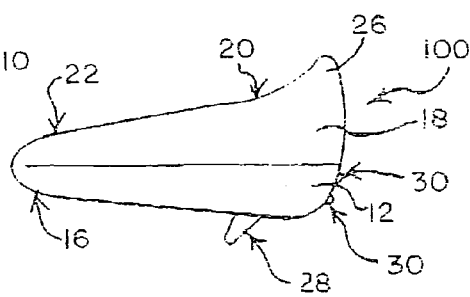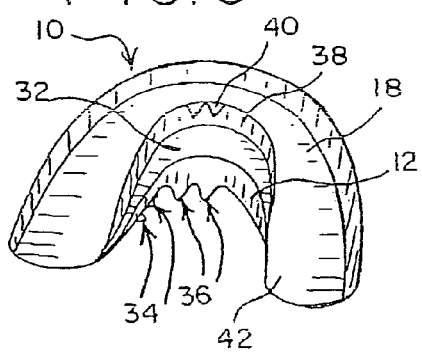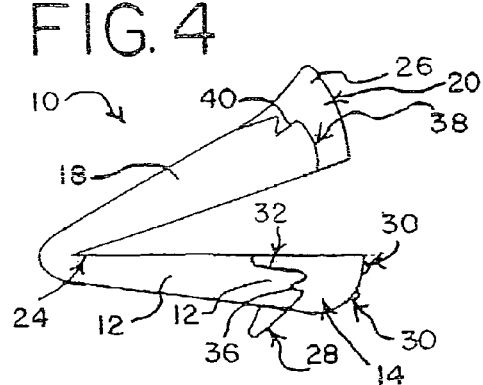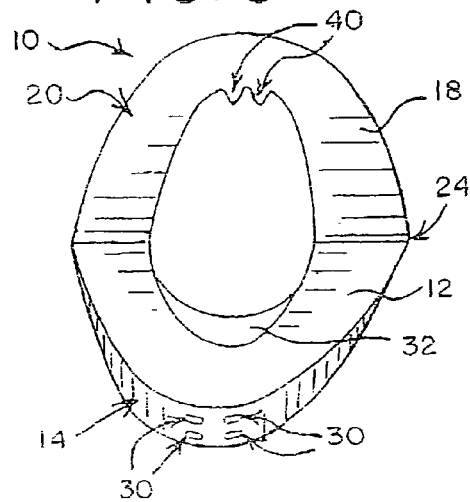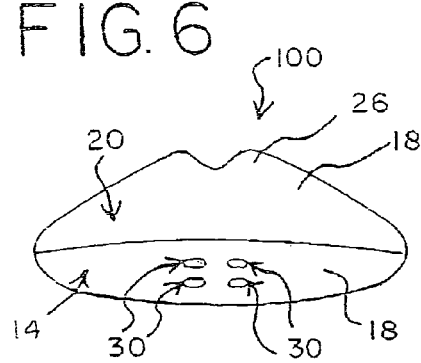

APPLIANCE, SYSTEM AND METHOD FOR CORRECTION HABITS OF AN ORAL CAVITY

This application claims the benefit of U.S. Provisional Application Ser. No. 60/792,729, filed Apr. 18, 2006.

BACKGROUND OF THE INVENTION

The present invention generally relates to an appliance, a system and a method for correcting habits of an oral cavity. More specifically, the present invention relates to an appliance, a system and a method for correcting habits of an oral cavity of a patient in resting periods which may prevent abnormal swallowing patterns, abnormal tongue posturing, abnormal lip posturing. Further, the appliance, the system and the method may prevent improper tongue placement and/or poor tongue coordination during speech. The appliance may be preformed or may be customized in a one-size-fits-all version or in various sizes for wearing the appliance on an upper dentition or on a lower dentition of the patient. The appliance may move and/or may maintain a tongue of a patient at an elevated position during swallowing movements by the patient.

A shelf may be formed in the appliance for preventing the tongue from moving into an abnormal position with respect to the lower jaw. The appliance may have one or more first projections which may extend inwardly with respect to the oral cavity and/or the tongue of the patient. The appliance may have one or more second projections which may extend rearwardly with respect to central incisors in the upper dentition of the patient. The appliance may have one or more slots for receiving the upper dentition of the patient. A front of the appliance may have one or more third projections which may extend inwardly with respect to a labial area of the patient. An upper front margin of the appliance may move and/or may maintain the appliance within a mouth of the patient as the mouth of the patient may open in a sleeping period of the patient. A lingual tab may be formed on the appliance for maintaining a lower jaw of the patient in a forward position with respect to an upper jaw of the patient.

It is generally known that a care provider, such as, for example, a dentist or an orthodontist examines teeth and/or a mouth of a patient to determine abnormal oral functions of the patient. The care provider provides an orthodontic appliance to be worn by a patient for correcting, for reducing and/or for minimizing the abnormal oral functions of the patient. The abnormal oral functions of the patient which may be correctable via the orthodontic appliance may be, for example, a finger sucking habit, a thumb sucking habit, abnormal swallowing patterns, abnormal tongue posturing, abnormal lip posturing, concommitant speech problems, poor tongue placement and/or poor tongue coordination.

For example, the patient may be a child having a thumb sucking habit and/or a finger sucking habit which may continue and/or may persist after adult front incisors erupt into a mouth of the child. The adult front incisors typically erupt as the child becomes seven (7) years old. The thumb sucking and/or the finger sucking after the adult front teeth erupt may result in abnormal tongue coordination by the child which is involved in abnormal swallowing patterns, concommitant speech problems and/or malocclusions of one or more teeth of the child. Further, the thumb sucking and/or the finger sucking prevents permanent incisors from fully erupting into a normal vertical position, into a normal horizontal position and/or into normal occlusal positions resulting in an open bite in the mouth of the child.

However, traditionally, the orthodontic appliance is a custom-made orthodontic appliance which is only capable of correcting, reducing and/or minimizing one of the abnormal oral functions of the patient. As a result, two or more orthodontic appliances are required to correct and/or to minimize more than one of the abnormal oral functions of the patient. Since the orthodontic appliance is custom-made, the orthodontic appliance is only capable of being worn by a single patient and may not be produced to be worn by one or more patients having various sizes and shapes of dentitions. Moreover, the orthodontic appliance may be expensive and/or may be inconvenient to produce and/or to manufacture because the orthodontic appliance must be customized to the dentition of each patient.

A need, therefore, exists for an appliance, a system and a method for correcting habits of an oral cavity. Additionally, a need exists for an appliance, a system and a method for correcting habits of an oral cavity which may be manufactured in a preformed version or in a custom-made version to be worn on a dentition of a patient. Further, a need exists for an appliance, a system and a method for correcting habits of an oral cavity which may correct, may treat, may reduce and/or may minimize more than one abnormal oral function of a patient. Still further, a need exists for an appliance, a system and a method for correcting habits of an oral cavity which may be manufactured and/or may be produced in a one-size-fits-all version or in various sizes to be worn on a dentition of a patient. Moreover, a need exists for an appliance, a system and a method for correcting habits of an oral cavity which may correct and/or may treat a finger sucking habit, a thumb sucking habit, abnormal swallowing patterns, abnormal tongue posturing, abnormal lip posturing, concommitant speech problems, poor tongue placement and poor tongue coordination. Furthermore, a need exists for an appliance, a system and a method for correcting habits of an oral cavity which may provide one or more slots, one or more projections, a lingual shelf, an upper front margin and/or a lingual tab to correct and/or to treat the habits of the oral cavity of a patient.

SUMMARY OF THE INVENTION

The present invention generally relates to an appliance, a system and a method for correcting habits of an oral cavity. More specifically, the present invention relates to an appliance, a system and a method for correcting habits of an oral cavity which may correct and/or may treat abnormal functions associated with the oral cavity of a patient. The abnormal functions may be related to and/or may correspond to a finger sucking habit, a thumb sucking habit, abnormal swallowing patterns, abnormal tongue posturing, abnormal lip posturing and/or concommitant speech problems. The orthodontic appliance may be a preformed appliance and/or a custom-made appliance which may move and/or may position a tongue of the patient in an elevated position during swallowing movements by the patient and/or during a resting periods between the swallowing movements by the patient.

A shelf may be formed on the orthodontic appliance which may prevent the tongue of the patient from moving to an abnormal position within the oral cavity of the patient. The shelf may prevent the tongue of the patient from moving to a depressed position and/or to a lowered position within a lower jaw and/or within a mandibular area in the oral cavity of the patient. During the resting periods and/or during the swallowing movements by the patient, the tongue of the patient should be in an elevated position within the oral cavity which may position the tongue against a palate of the patient and/or within an upper jaw of and/or within a maxilla area of the oral cavity of the patient. The orthodontic appliance prevents the tongue of the patient from moving to the abnormal position within the oral cavity of the patient. The patient typically may swallow about two (2) times per minute during waking hours and about one (1) time per minute during sleeping hours. Use of the orthodontic appliance by the patient may teach and/or may train the patient to properly position the tongue in the elevated position within the oral cavity of the patient with or without wearing the orthodontic appliance.

First projections may be formed in the orthodontic appliance which may extend from the orthodontic appliance outwardly with respect to the oral cavity of the patient and/or to the tongue of the patient. The first projections may contact and/or may abut the tongue of the patient to remind the patient that the tongue is in an abnormal position within the oral cavity of the patient. The first projections may make the patient uncomfortable when the tongue is in the abnormal position within the oral cavity of the patient. As a result, the patient may elevate the tongue within the oral cavity to move the tongue from the abnormal position and/or the improper position to a correct position within the oral cavity of the patient. The correct position of the tongue within the oral cavity of the patient may be above and/or adjacent to the shelf of the orthodontic appliance. The shelf and/or the first projections may encourage the patient to move the tongue to a normal position during the swallowing movements by the patient in a daytime period and/or during the resting periods between swallowing movements and/or also during sleeping periods.

Second projections may be formed in the orthodontic appliance which may extend outwardly from the orthodontic appliance behind upper incisors of an upper dentition of the patient. The second projections may move and/or may position a tip of the tongue of the patient to a correct position within the oral cavity of the patient during the swallowing movements by the patient. The correct position for the tip of the patient may be behind and/or may be adjacent to the second projections of the orthodontic appliance. The orthodontic appliance may prevent tongue thrusting by the patient during the resting periods by the patient and/or during the swallowing movements by the patient. Moreover, the correct position of the tip of the tongue may be behind a maxillary rugae and/or behind elevations of a palatal tissue which may be immediately behind the upper central incisors at a midline of the upper dentition of the patient.

The orthodontic appliance may train the patient to breathe through a nose of the patient instead of through the mouth of the patient. Breathing through the mouth of the patient may result in the patient having the abnormal breathing patterns and/or having difficulty learning to breathe through the nose of the patient. A front of the orthodontic appliance may open to allow the patient to breathe through the mouth of the patient to adapt to wearing and/or with using the orthodontic appliance. A closed version of the orthodontic appliance may be worn by the patient to force the patient to breathe through the nose of the patient instead of the mouth of the patient. The orthodontic appliance may train the patient to habitually breathe properly through the nose of the patient.

The orthodontic appliance may be preformed or may be custom made to the mouth and/or to the dentition of the patient. The orthodontic appliance may be manufactured in a one-size-fits-all version or in various sizes. In the one-size-fits-all version, the orthodontic appliance may have a slot without sockets for receiving one or more teeth of the patient. Further, the slot may receive teeth of patients of all ages. In various sizes, orthodontic appliances may be preformed to receive one or more teeth of various sizes from patients having various ages.

Third projections may be formed on the front of the orthodontic appliance to maintain lips of the patient in a closed position during the swallowing movements by the patient. The orthodontic appliance may have an upper front margin to maintain the orthodontic appliance in the mouth of the patient. The upper front margin may prevent the orthodontic appliance from moving rearward in the mouth of the patient when the mouth of the patient may be opened during sleeping periods of the patient. The orthodontic appliance may have an extended lingual tab to maintain the lower jaw of the patient in a forward position with respect to the upper jaw of the patient. The elevated upper front margin and/or the extended lingual tab may correct and/or may treat overjets, protruding upper front teeth and/or small receding lower jaws in the mouth of the patient.

It is, therefore, an advantage of the present invention to provide an appliance, a system and a method for correcting habits of an oral cavity.

Another advantage of the present invention is to provide an appliance, a system and a method for correcting habits of an oral cavity which may provide a preformed or a custom-made orthodontic appliance with or without sockets to train a tongue of a patient and/or a musculature of the patient for functioning normally during swallowing, during resting posture and/or during speech by the patient.

And, another advantage of the present invention is to provide an appliance, a system and a method for correcting habits of an oral cavity which may provide a one-size-fits-all dental appliance or dental appliances of various sizes to train a tongue of a patient and/or a musculature of the patient for functioning during swallowing, during resting posture and/or during speech by the patient.

Yet another advantage of the present invention is to provide an appliance, a system and a method for correcting habits of an oral cavity which may provide a shelf and/or one or more protrusions to guide a tongue of a patient and/or lips of the patient for functioning normally during swallowing, during resting posture and/or during speech.

A further advantage of the present invention is to provide an appliance, a system and a method for correcting habits of an oral cavity which provides a shelf and/or one or more protrusions to train a tongue of a patient for functioning normally during swallowing in the daytime or in the nighttime.

Moreover, an advantage of the present invention is to provide an appliance, a system and a method for correcting habits of an oral cavity which provides a shelf and/or one or more protrusions to properly position of a tongue of a patient during swallowing movements by the patient.

And, another advantage of the present invention is to provide an appliance, a system and a method for correcting habits of an oral cavity which may provide a shelf and/or one or more protrusions to encourage a patient to breathe through a nose of the patient.

Yet another advantage of the present invention is to provide an appliance, a system and a method for correcting habits of an oral cavity which provide a shelf and/or one or more protrusions to discourage a patient to breathe through a mouth of the patient.

Another advantage of the present invention is to provide an appliance, a system and a method for correcting habits of an oral cavity which may provide a shelf and/or one or more protrusions to improve a position of a tongue of a patient within an oral cavity of the patient during speech and/or during pronouncement of fricative sounds by the patient.

Yet another advantage of the present invention is to provide an appliance, a system and a method for correcting habits of an oral cavity which may provide a shelf and/or one or more protrusions to move lips of a patient in a correction position during swallowing movements by the patient.

A still further advantage of the present invention is to provide an appliance, a system and a method for correcting habits of an oral cavity which may encourage nasal breathing by a patient and/or may discourage breathing through the oral cavity by the patient.

Moreover, an advantage of the present invention is to provide an appliance, a system and a method for correcting habits of an oral cavity which may provide a shelf and/or one or more protrusions to terminate and/or to stop a thumb sucking habit of a patient and/or a finger sucking habit of the patient.

And, another advantage of the present invention is to provide an appliance, a system and a method for correcting habits of an oral cavity which may provide a shelf and/or one or more protrusions to advance a lower jaw of a patient with respect to an upper jaw of the patient.

Yet another advantage of the present invention is to provide an appliance, a system and a method for correcting habits of an oral cavity which may provide a shelf and/or one or more protrusion to correct and/or to treat overjets within a mouth of the patient.

Another advantage of the present invention is to provide an appliance, a system and a method for correcting habits of an oral cavity which may provide a shelf and/or one or more protrusions for encouraging a tongue of a patient to move to an elevated posture with respect to a lower dentition of the patient during resting periods by the patient and/or during swallowing movements by the patient.

Yet another advantage of the present invention is to provide an appliance, a system and a method for correcting habits of an oral cavity which may provide a shelf and/or one or more protrusions to prevent a tongue of a patient from protruding between upper front teeth of the patient and lower front teeth of the patient at a resting posture of the patient.

A still further advantage of the present invention is to provide an appliance, a system and a method for correcting habits of an oral cavity which may provide a shelf and/or one or more protrusions to correct, to relieve and/or to treat temporomandiular joint (hereinafter "TMJ") problems of a patient.

Moreover, an advantage of the present invention is to provide an appliance, a system and a method for correcting habits of an oral cavity which may relieve, may treat and/or may correct muscular aches from TMJ problems of a patient.

And, another advantage of the present invention is to provide an appliance, a system and a method for correcting habits of an oral cavity which may provide a shelf and/or one or more protrusions to relieve malocclusions problems of a patient.

Yet another advantage of the present invention is to provide an appliance, a system and a method for correcting habits of an oral cavity which may correct and/or may treat tongue malfunctions, such as, for example, a narrowed upper arch, protrusive upper incisors, a protrusive upper jaw of a patient.

Another advantage of the present invention is to provide an appliance, a system and a method for correcting habits of an oral cavity which may provide a shelf and/or one or more protrusions to prevent a permanent open-bite from developing in a mouth of a patient.

Yet another advantage of the present invention is to provide an appliance, a system and a method for correcting habits of an oral cavity which may provide a shelf and/or one or more protrusions to correct and/or to treat an open bite malocclusion in a mouth of a patient.

A still further advantage of the present invention is to provide an appliance, a system and a method for correcting habits of an oral cavity which may correct and/or may treat abnormal swallowing patterns, abnormal tongue posturing and/or abnormal lip posturing within the oral cavity of the patient.

Moreover, an advantage of the present invention is to provide an appliance, a system and a method for correcting habits of an oral cavity which may correct and/or may treat abnormal habits in the oral cavity of a patient during resting periods between swallowing movements by the patient.

And, another advantage of the present invention is to provide an appliance, a system and a method for correcting habits of an oral cavity which may correct and/or may treat concomitant speech problems involving fricatives due to poor tongue placement and/or poor tongue coordination.

Yet another advantage of the present invention is to provide an appliance, a system and a method for correcting habits of an oral cavity which may provide one or more protrusion to move a tip of a tongue of a patient to a correct position within a mouth of the patient.

Another advantage of the present invention is to provide an appliance, a system and a method for correcting habits of an oral cavity may prevent tongue thrusting by a tongue of a patient during resting periods and/or during swallowing movements by the patient.

Yet another advantage of the present invention is to provide an appliance, a system and a method for correcting habits of an oral cavity which may provide an elevated upper front margin to maintain the appliance in a mouth of a patient when the mouth of the patient may be in an open position.

A still further advantage of the present invention is to provide an appliance, a system and a method for correcting habits of an oral cavity which may provide an extended lingual tab to move a lower jaw of a patient to a forward position with respect to an upper jaw of the patient.

Additional features and advantages of the present invention are described in, and will be apparent from, the detailed description of the presently preferred embodiments and from the drawings.

BRIEF DESCRIPTION OF THE DRAWINGS

FIG. 1 illustrates a side view of an appliance in an open position in an embodiment of the present invention.

FIG. 2 illustrates a side view of an appliance in a closed position in an embodiment of the present invention.

FIG. 3 illustrates a rear perspective view of an appliance in the closed position in an embodiment of the present invention.

FIG. 4 illustrates a side cutout view of an appliance in the open position with a midline cut in an embodiment of the present invention.

FIG. 5 illustrates a front perspective view of an appliance in the open position in an embodiment of the present invention.

FIG. 6 illustrates a front view of an appliance in the closed position in an embodiment of the present invention.

DETAILED DESCRIPTION OF THE PRESENTLY PREFERRED EMBODIMENTS

The present invention generally relates to an appliance, a system and a method for correcting habits of an oral cavity. More specifically, the present invention relates to an appliance, a system and a method for correcting habits of an oral cavity of a patient which may be preformed or may be custom-made in an open position or in a closed position. The appliance may prevent the patient from breathing through an oral cavity of the patient to encourage the patient to breathe through a nose of the patient. The appliance may correct and/or may treat abnormal swallowing patterns, finger sucking habits, thumb sucking habits, abnormal tongue posturing, abnormal lip posturing and/or speech problems of the patient. A slot may be formed on a top portion of the appliance to receive one or more teeth of the patient for wearing the appliance in the oral cavity of the patient. A shelf may be formed on a bottom portion of the appliance to move a tongue of the patient to a correct position within the oral cavity of the patient during swallowing movements by the patient and/or during resting periods between the swallowing movements of the patient. First projections may be formed on the appliance which may contact the tongue of the patient to move the tongue of the patient to the correct position within the oral cavity of the patient. Second projections may be formed on the appliance which may contact the tongue of the patient to prevent tongue thrusting by the patient during the resting periods and/or during the swallowing movements by the patient. Third projections may be formed on the appliance to move lips of the patient to a closed position during the swallowing movement by the patient. An upper front margin may be formed on the top portion of the appliance to maintain the appliance within the oral cavity of the patient for opening a mouth of the patient. A lingual tab may be formed on the bottom portion of the appliance to move a lower jaw of the patient to a forward position with respect to an upper jaw of the patient.

Referring now to the drawings wherein like numerals refer to like parts, FIG. 1 illustrates an appliance 10 in an open position for correcting a habit of an oral cavity of a patient (not shown in the figures) in an embodiment of the present invention. FIG. 2 illustrates an appliance 100 in a closed position for correcting the habit of the oral cavity of the patient in an embodiment of the present invention. The appliance 10 and/or the appliance 100 (collectively known hereinafter as "the appliances 10, 100") may be worn in the mouth of and/or in the oral cavity of the patient for correcting the habit of the oral cavity. The appliances 10, 100 may be worn on a dentition of the patient to correct the habit of the oral cavity.

The dentition of the patient may include upper teeth and/or lower teeth. The patient may have an upper jaw and/or a lower jaw. The upper jaw may have an arch which may have the upper teeth thereon. The upper teeth of the patient may erupt and/or may extend outward or downward with respect to the arch of the upper jaw. The lower jaw may have an arch which may have the lower teeth thereon. The lower teeth of the patient may erupt and/or may extend outward or upward with respect to the arch of the lower jaw.

The appliances 10, 100 may have a lower portion 12 which may abut and/or may contact tops of the lower teeth of the patient. The lower portion 12 may be, for example, flat and/or indented to accommodate and/or to receive occlusal surfaces of the lower teeth. The appliances 10, 100 may have an upper portion 18 which may abut and/or may contact tops of the upper teeth of the patient. The upper portion 18 may be, for example, flat and/or indented to accommodate and/or to receive occlusal surfaces of the upper teeth.

The lower portion 12 of the appliances 10, 100 may have a front end 14 and a rear end 16 which is opposite to front end 14 of the appliance 10, 100. The upper portion 18 of the appliances 10, 100 may have a front end 20 and a rear end 22 which is opposite to the front end 20 of the appliances 10, 100.

The front end 14 of the appliances 10, 100 may be adjacent to and/or may abut the front end 20 of the appliances 10, 100. The rear end 16 of the appliances 10, 100 may be adjacent to and/or may abut the rear end 22 of the appliances 10, 100.

The appliance 10 may have a hinge 24 for connecting and/or for attaching the lower portion 12 and the upper portion 18 as illustrated in FIGS. 1, 4 and 5. The hinge 24 may attach and/or may connect the rear end 16 of the lower portion 12 to the rear end 22 of the upper portion 18. The hinge 24 may be integrally formed with the appliance 10. The front end 20 of the upper portion 18 may move inwardly and/or may move outwardly with respect to the front end 14 of the lower portion 12. The upper portion 18 may rotate, may pivot and/or may move inwardly or outwardly with respect to the lower portion 12 via the hinge 24. As a result, the appliance 10 may be formed in the open position.

As shown in FIGS. 2, 3 and 6, the lower portion 12 may be attached to and/or may be connected to the upper portion 14 of the appliance 100. As a result, the lower portion 12 may not be separable and/or may not be movable with respect to the upper portion 18. The lower portion 12 of the appliance 100 may be integrally formed with the upper portion 18. As a result, the appliance 100 may be formed in the closed position.

The appliances 10, 100 may be constructed from, for example, rubber, plastic, polyurethane, polyethylene, polypropylene and/or polyvinyl-chloride. Further, the appliances 10, 100 may be constructed from, for example, a stiff polymer material, a soft polymer material, a combination of both a stiff polymer material and/or a soft polymer material. It should be understood that the appliances 10, 100 may be constructed from any material as known by one of ordinary skill in the art.

The appliance 10 may be preformed or may be custom-made in the open position to be worn on the dentition of the patient as shown in FIGS. 1, 4 and 5. As a result, the appliance 10 may be sized to receive the dentition of the patient. The appliance 10 may be formed in a one-size-fits-all version which may be sized to be worn on the dentition of the patient. The appliance 10 may be formed in various sizes which may correspond to and/or may be based on dentitions of one or more patients (not shown in the figures). As a result, the appliance 10 may be worn on dentitions of various sizes by patients of various ages.

The appliance 100 may be preformed or may be custom-made in the closed position to be worn on the dentition of the patient as shown in FIGS. 2, 3 and 6. As a result, the appliance 100 may be sized to receive the dentition of the patient. The appliance 100 may be formed in a one-size-fits-all version which may be sized to be worn on the dentition of the patient. The appliance 100 may be formed in the various sizes which may correspond to and/or may be based on the dentitions of one or more patients. As a result, the appliance 100 may be worn on dentitions of various sizes by patients of various ages.

The oral cavity of the patient may exhibit and/or may demonstrate abnormal functions associated with swallowing, sucking, tongue position, lip position and/or speech problems. The abnormal functions may include, for example, abnormal swallowing patterns, abnormal tongue posturing, abnormal lip posturing, concomitant speech problems, improper tongue placement, improper tongue coordination, nasal breathing, thumb sucking habits, finger sucking habits and/or the like. The abnormal swallowing patterns, the abnormal tongue posturing and/or the abnormal lip posturing may occur within the oral cavity of the patient during resting periods when the patient may not be swallowing, may not be speaking and/or may not be eating. The improper tongue placement and/or the improper tongue coordination may result in the patient having concommitant speech problems during speech. The dentition of the patient may exhibit and/or may demonstrate an orthodontic condition, such as, for example, open bite, overjet, malocclusion, tongue thrusting, protruding upper incisors, protruding upper jaw, narrowed upper arch, receding low jaw and/or the like.

As shown in FIGS. 1, 2, 4 and 6, an upper margin 26 may be formed on and/or may be attached to the front end 20 of the upper portion 18 of the appliances 10, 100. The upper margin 26 may be integrally formed with the appliances 10, 100. The upper margin 26 may be located above and/or may be elevated above the upper front incisors of the patient when the appliances 10, 100 may be worn in the oral cavity of the patient. The upper margin 26 may be located between and/or may be positioned between the upper front incisors and the upper lip of the patient. The upper margin 26 may maintain the appliances 10, 100 within the oral cavity of the patient when the oral cavity of the patient may be opened such as when the patient may be sleeping. The upper margin 26 may prevent the appliances 10, 100 from moving rearward with respect to the oral cavity of the patient by abutting and/or by contacting the inner front incisors of the patient. As a result, the appliance 10, 100 may be retained within the oral cavity of the patient by the upper margin 26 of the upper portion 18 of the appliances 10, 100.

The front end 20 of the upper portion 18 may separate from the front end 14 of the lower portion 12 via the hinge 24. Separation of the upper portion 18 and the lower portion 12 via the hinge 24 may prevent the appliance 10 from being removed from the oral cavity of the patient when the mouth of the patient may be opened such as when the patient may be sleeping. As a result, the appliance 10 may be maintained and/or may be retained within the oral cavity of the patient via the hinge 24.

As shown in FIGS. 1-4, a lingual tab 28 may be formed on and/or may be attached to the lower portion 12 of the appliances 10, 100. The lingual tab 28 may be integrally formed with the appliances 10, 100. The lingual tab 28 may extend downwardly with respect to the lower portion 12 when the appliances 10, 100 may be worn within the oral cavity of the patient. The lingual tab 28 may contact and/or may be adjacent to the lower jaw of the patient for moving the lower jaw to a correct position with respect to the upper jaw of the patient. The lingual tab 28 may move the lower jaw of the patient forward within the oral cavity to position the lower jaw in the correct position with respect upper jaw of the patient. As a result, the upper margin 26 and/or the lingual tab 28 may correct and/or may treat an overjet, protruding upper front teeth and/or a receding lower jaw in the dentition of the patient.

As shown in FIGS. 1, 2 and 4-6, lower labial protrusions 30 may be formed on and/or may be attached to the front end 14 of the lower portion 12 of the appliances 10, 100. The lower labial protrusions 30 may be integrally formed with the appliances 10, 100. The lower labial protrusions 30 of the appliances 10, 100 may be adjacent to, may contact and/or may abut a lower lip of the patient. The patient may experience discomfort from the lower labial protrusions 30 contacting the lower lip when the lower lip may be separated from the upper lip of the patient. As a result, the lower labial protrusions 30 may prevent the patient from separating the lower lip and the upper lip (collectively known hereinafter as "the lips") of the patient to encourage the patient to maintain the lower lip in a correct position. Further, the lower labial protrusions 30 may remind the patient to move the lips of the patient to the correct position during closure of the oral cavity and/or during wear of the appliance 100 in the closed position. Moreover, the lower labial protrusions 30 may encourage the patient to move the lips of the patient to the correct position during the swallowing movements by the patient and/or during the resting periods between the swallowing movements by the patient.

As shown in FIGS. 3-5, a shelf 32 may be formed in and/or may be attached to the lower portion 12 of the appliances 10, 100. The shelf 32 may be integrally formed with the appliances 10, 100. The shelf 32 may extend rearwardly from the front end 14 of the lower portion 12 of the appliances 10, 100 to reduce an area which may be available for receiving the tongue of the patient. Lingual side protrusions 34 and/or lingual front protrusions 36 (collectively known hereinafter as "the lingual protrusions 34, 36") may be formed on and/or may be attached to shelf 32 and/or to the lower portion 12 of the appliances 10, 100. The lingual protrusions 34, 36 may be integrally formed with the appliances 10, 100. The lingual protrusions 34, 36 may be adjacent to, may contact and/or may abut the tongue of the patient to discourage the patient from resting the tongue on the shelf 32 and/or in the lower portion 12 of the appliances 10, 100. The lingual front protrusions 36 may be located at a midline (not shown in the figures) of the appliances 10, 100.

The patient may experience discomfort from the lingual protrusions 34, 36 contacting the tongue of the patient to prevent the patient from resting the tongue on the shelf 32 and/or in the lower portion 12 of the appliances 10, 100. The patient may move the tongue to an elevated position respect to the lower jaw of the patient, the lower teeth of the patient and/or the lower portion 12 of the appliances 10, 100 to avoid discomfort from the lingual protrusions 34, 36. As a result, the lingual protrusions 34, 36 may encourage the patient to move and/or to maintain the tongue in the elevated position within the oral cavity of the patient.

A hollowed area 38 may be formed in the upper portion 18 of the appliances 10, 100 as shown in FIGS. 3 and 4 for receiving the tongue of the patient. The hollowed area 38 may be adjacent to the upper teeth of the patient and/or the upper jaw of the patient when the appliances 10, 100 may be worn in the oral cavity of the patient. The hollowed area 38 may encourage the patient to position the tongue of the patient within the upper arch of the oral cavity of the patient to prevent placement of the tongue within the lower arch of the dentition of the patient, since there is more room available in the upper arch than in the lower arch.

Lingual top protrusions 40 may be formed in and/or may be attached to the upper portion 18 of the appliances 10, 100 which may be positioned at the midline of the appliances 10, 100. The lingual top protrusions 40 may be integrally formed with the appliances 10, 100. The lingual top protrusions 40 may be adjacent to, may contact and/or may abut a tip of the tongue of the patient when the tongue may be located within the hollowed area 38 of the upper portion 18 of the appliances 10, 100. The patient may experience discomfort from the lingual top protrusion 40 contacting the tip of the tongue of the patient to prevent the tongue from being positioned in a front of the oral cavity of the patient. The lingual top protrusions 40 may remind the patient that the tip of tongue should not be position within the front of the oral cavity during the swallowing movements by the patient and/or during the resting period between the swallowing movements by the patient.

The lingual top protrusions 40 may prevent tongue thrusting by the tongue of the patient within the oral cavity during the swallowing movements by the patient. Further, the lingual top protrusions 40 may prevent tongue thrusting by the tongue of the patient within the oral cavity during the resting periods between the swallowing movements by the patient. Still further, the lingual top protrusions 40 may move and/or may maintain the tip of the tongue at a correction position which may be behind a maxillary rugae within the oral cavity of the patient or adjacent to elevations of tissue behind the inner front incisors in the oral cavity of the patient.

The patient may exhibit and/or may have a finger sucking habit and/or a thumb sucking habit. As a result, the patient may insert and/or may place a finger of the patient and/or a thumb of the patient within the oral cavity of the patient which may contact the inner front incisors of the patient. The finger and/or the thumb of the patient may be adjacent to, may contact and/or may abut the lingual top protrusions 40 of the appliance 10 when the appliance 10 may be worn by the patient. The patient may experience discomfort from the lingual top protrusions 40 contacting the finger or the thumb of the patient to prevent the finger sucking habit and/or the thumb sucking habit by the patient. As a result, the lingual top protrusions 40 of the appliance may encourage the patient to terminate and/or to end the finger sucking habit and/or the thumb sucking habit.

The appliances 10, 100 may train the patient to breathe through a nose of the patient to prevent the patient from breathing through the oral cavity of the patient. The patient which may breathe through the mouth and/or the oral cavity without breathing through the nose of the patient may wear the appliance 10 to encourage nasal breathing. The appliance 10 in the open position may allow the patient to breathe through the oral cavity of the patient for adapting to the appliance 10 and/or for nasal breathing. The patient may wear the appliance 100 in the closed position to prevent the patient from breathing through the mouth of the patient to encourage nasal breathing by the patient. As a result, the patient may be required to nasal breathe by wearing the appliance 100 in the closed position to breathe properly through the nose of the patient.

In an embodiment, a slot 42 may be formed in the lower portion 12 and/or in the upper portion 18 of the appliances 10, 100 as shown in FIG. 3 for wearing the appliances 10, 100 on the dentition within the oral cavity of the patient. The slot 42 may be preformed or may be custom-made to receive the upper teeth or the lower teeth of the patient when the patient may be wearing the appliances 10, 100. The slot 42 may be adjacent to, may contact and/or may abut the tops of the upper teeth or the lower teeth of the patient when the patient may be wearing the appliances 10, 100. The lower teeth or the upper teeth of the patient may be inserted into the slot 42 of the lower portion 12 or the upper portion 18, respectively, when the appliances 10, 100 may be worn in the oral cavity by the patient.

The slot 42 may provide one or more sockets (not shown in the figures) to receive one or more of the lower teeth or the upper teeth of the patient to wear the appliances 10, 100 within the oral cavity of the patient. Alternatively, the slot 42 may be partitioned into two or more slots (not shown in the figures) to receive one or more of the lower teeth or of the upper teeth of the patient to wear the appliances 10, 100 within the oral cavity of the patient. As a result, the slot 42 of the appliances 10, 100 may be customized to the dentition of the patient to provide a comfortable orthodontic appliance for correcting and/or for treating abnormal functions within the oral cavity of the patient.

The appliances 10, 100 may correct and/or may treat the habits and/or the abnormal functions of the patient in the oral cavity. The appliances 10, 100 may prevent the patient from breathing through the oral cavity to encourage the patient to breathe through the nose of the patient. The shelf 32 may be formed on the bottom portion 12 of the appliances 10, 100 to move the tongue of the patient to the correct position within the oral cavity of the patient during the swallowing movements by the patient and/or during the resting periods between the swallowing movements of the patient.

The lingual projections 34, 36 may be formed on the appliances 10, 100 which may contact the tongue of the patient to move the tongue of the patient to the correct position within the oral cavity of the patient. Lingual top projections 40 may be formed on the appliances 10, 100 which may contact the tongue of the patient to prevent tongue thrusting by the tongue of the patient during the resting periods and/or during the swallowing movements by the patient. The lower labial projections 30 may be formed on the appliances 10, 100 to move the lips of the patient to the closed position during the swallowing movement by the patient.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. An orthodontic system worn adjacent to upper teeth and lower teeth in a mouth of a user wherein the user has an upper jaw, a lower jaw, lips and a tongue, the orthodontic system comprising:

an upper dental appliance having a front end and a rear end wherein the rear end is located in a position opposite to the front end wherein the upper dental appliance has a U-shape and further wherein the upper dental appliance is adapted to contact the upper teeth;

a lower dental appliance having a front end and a rear end wherein the rear end is located in a position opposite to the front end wherein the lower dental appliance has a U-shape and further wherein the lower dental appliance has a lower flat surface adapted to contact the lower teeth wherein the lower dental appliance has an upper flat surface located in a position opposite to the lower surface;

first lingual projections that extend horizontally from the lower dental appliance wherein the first lingual projections extend from a section of the lower dental appliance that is adjacent to the rear end of the lower dental appliance wherein each of the first lingual projections has an end portion farthest from the lower dental appliance wherein the end portion of each of the first lingual projections is adapted to contact the tongue of the user;

second lingual projections that extend horizontally from the front end of the lower dental appliance in a direction rearward in the mouth wherein each of the second lingual projections has an end portion farthest from the lower dental appliance wherein the end portion of each of the second lingual projections is adapted to contact the tongue of the user and further wherein each of the second lingual projections has a width that decreases continuously as each of the second projections extends from the lower dental appliance; and a shelf connected to the lower dental appliance wherein the shelf extends from the lower dental appliance and further wherein the shelf is adapted to extend rearward in the mouth of the user wherein the shelf has a horizontal planar surface that is adapted to contact the tongue and further wherein the horizontal planar surface is substantially coplanar with the upper flat surface of the front end of the lower dental appliance.

2. The system of claim 1 further comprising:
a first lingual tab that projects downward from the front end of the lower dental appliance wherein the first lingual tab is adapted to move the lower jaw to a position relative to the upper jaw.

3. The system of claim 1 further comprising:
an upper margin on the upper dental appliance that is adapted to extend vertically from the upper dental appliance to a point above the upper teeth of the user.

4. The system of claim 1 further comprising:
lower labial protrusions that extend from the front end of the lower dental appliance wherein the lower labial protrusions are adapted to extend forward relative to the mouth of the user.

5. The system of claim 1 wherein the shelf is coplanar with the upper flat surface of the front area of the lower dental appliance.

6. The system of claim 1 further comprising:
an indentation in the front end of the upper dental appliance wherein the indentation is adapted to move the tongue to an elevated position.

7. The system of claim 1 further comprising:
upper lingual protrusions that extend from the front end of the upper dental appliance wherein the upper lingual protrusions are adapted to extend rearward relative to the mouth of the user to contact the tongue of the user and further wherein each of the upper lingual protrusions has a substantially triangular shape.

8. The system of claim 1 further comprising:
a slot formed in the upper dental appliance wherein the slot is adapted to receive the upper teeth of the user.

9. An orthodontic appliance for correcting an abnormal habit in a mouth of a user wherein the user has lips, a tongue and incisors, the appliance comprising:
a generally U-shaped upper portion having a front end and a rear end wherein the rear end is located in a position opposite to the front end wherein the front end of the upper portion is adapted to be located adjacent to the incisors;
a generally U-shaped lower portion having a front end and a rear end wherein the rear end is located in a position opposite to the front end wherein the front end of the lower portion is adapted to be located adjacent to the incisors;
an indentation in the upper portion wherein the indentation is shaped to receive the tongue of the user to maintain the tongue in an elevated position;
first lingual projections that extend from the lower portion wherein the first lingual projections extend horizontally from a section of the lower portion that is located in a position rearward in the mouth relative to the front end of the lower portion wherein each of the first lingual projections has an end portion farthest from the lower portion wherein the end portion of each of the first lingual projections is adapted to contact the tongue of the user;
second lingual projections that extend horizontally from the front end of the lower dental appliance in a direction rearward in the mouth wherein each of the second lingual projections has an end portion farthest from the lower dental appliance and further wherein the end portion of each of the second lingual projections is adapted to contact the tongue of the user; and
a shelf connected to the lower portion wherein the shelf extends from the lower portion and further wherein the shelf is adapted to extend rearward in the mouth of the user in a direction which is horizontal and not vertical wherein the shelf has a horizontal planar surface that is adapted to contact the tongue.

10. The appliance of claim 9 further comprising:
an upper margin connected to the upper portion that is adapted to extend vertically from the upper portion to a point above the upper teeth of the user.

11. The appliance of claim 9 further comprising:
a lingual tab extending downwardly from the front end of the lower portion.

12. The appliance of claim 9 wherein the upper portion is maintained in a closed position relative to the lower portion wherein the front end of the upper portion is located adjacent to the front end of the lower portion in the closed position.

13. The appliance of claim 9 further comprising:
labial protrusions that extend from the front end of the lower portion wherein the labial protrusions are adapted to project in a forward direction relative to the mouth and further wherein the labial protrusions are adapted to contact the lips of the user.

14. An orthodontic system worn adjacent to upper teeth and lower teeth in a mouth of a user wherein the user has an upper jaw, a lower jaw, lips and a tongue, the orthodontic system comprising:
a dental appliance having an upper portion and a lower portion wherein the dental appliance has a U-shape and further wherein the dental appliance has a front end and a rear end located in a position opposite to the front end wherein the upper portion is adapted to contact the upper teeth wherein the lower portion is adapted to contact the lower teeth wherein the front end of the lower portion has an upper surface and a lower surface wherein the upper surface is located in a position opposite to the lower surface;
first lingual projections that extend horizontally from the dental appliance wherein the first lingual projections extend from a section of the dental appliance that is located in a position rearward in the mouth relative to the front end of the dental appliance wherein each of the first lingual projections has an end portion farthest from the dental appliance wherein the end portion of each of the first lingual projections is adapted to contact the tongue of the user;
second lingual projections that extend horizontally from the dental appliance in a direction rearward in the mouth wherein each of the second lingual projections has an end portion farthest from the dental appliance wherein the end portion of each of the second lingual projections is adapted to contact the tongue of the user wherein each of the second lingual projections has a substantially triangular shape; and
a shelf connected to the lower portion wherein the shelf extends from the lower portion and further wherein the shelf is adapted to extend rearward in the mouth of the user wherein the shelf has a horizontal planar surface that is adapted to contact the tongue and further wherein the horizontal planar surface is coplanar with the upper surface of the front end of the lower portion.

15. The system of claim 14 further comprising:
a first lingual tab that projects downward from the lower portion wherein the first lingual tab is adapted to move the lower jaw to a position relative to the upper jaw.

16. The system of claim 14 further comprising:
an upper margin connected to the upper portion that is adapted to extend vertically from the upper portion to a point above the upper teeth of the user.

17. The system of claim 14 further comprising:
lower labial protrusions that extend from the lower portion wherein the lower labial protrusions are adapted to extend forward relative to the mouth of the user.

18. The system of claim 14 wherein the shelf is coplanar with the upper surface of the front end of the lower portion.

19. The system of claim 14 further comprising:
an indentation in the upper portion wherein the indentation is adapted to move the tongue to an elevated position.

20. The system of claim 14 further comprising:
upper lingual protrusions that extend from the upper portion wherein the upper lingual protrusions are adapted to extend rearward relative to the mouth of the user to contact the tongue of the user and further wherein each of the upper lingual protrusions has a substantially triangular shape.

* * * * *